(12) United States Patent
Brereton et al.

(10) Patent No.: US 10,542,777 B2
(45) Date of Patent: Jan. 28, 2020

(54) APPARATUS FOR HEATING OR COOLING A MATERIAL CONTAINED THEREIN

(71) Applicant: British American Tobacco (Investments) Limited, London (GB)

(72) Inventors: Simon Brereton, London (GB); Graham Plews, London (GB); Mark Forster, London (GB); Richard Pike, London (GB)

(73) Assignee: British American Tobacco (Investments) Limited, London (GB)

( * ) Notice: Subject to any disclaimer, the term of this patent is extended or adjusted under 35 U.S.C. 154(b) by 369 days.

(21) Appl. No.: 15/321,497

(22) PCT Filed: Jun. 26, 2015

(86) PCT No.: PCT/EP2015/064595
§ 371 (c)(1),
(2) Date: Dec. 22, 2016

(87) PCT Pub. No.: WO2015/197852
PCT Pub. Date: Dec. 30, 2015

(65) Prior Publication Data
US 2017/0196262 A1    Jul. 13, 2017

Related U.S. Application Data

(63) Continuation-in-part of application No. PCT/EP2014/063785, filed on Jun. 27, 2014.

(30) Foreign Application Priority Data

Jan. 14, 2015 (GB) .................................. 1500582.0

(51) Int. Cl.
*F25D 5/00* (2006.01)
*A24F 47/00* (2006.01)
*F25D 5/02* (2006.01)

(52) U.S. Cl.
CPC .............. *A24F 47/006* (2013.01); *F25D 5/02* (2013.01)

(58) Field of Classification Search
CPC ........ A24F 47/006; A61F 7/0241; A61F 7/03; A61F 7/106; A61F 2007/0276; A61F 2007/0292; A61F 2007/0293; F25D 5/02
(Continued)

(56) References Cited

U.S. PATENT DOCUMENTS 2,462,563 A   2/1949 Seyforth
2,689,150 A   9/1954 Corce
(Continued)

FOREIGN PATENT DOCUMENTS

AT   262137   5/1968
AT   306224   3/1973
(Continued)

OTHER PUBLICATIONS

Chinese Office Action, Application No. 201580034981.4, dated Aug. 3, 2018, 21 pages.
(Continued)

*Primary Examiner* — Claire E Rojohn, III
(74) *Attorney, Agent, or Firm* — Patterson Thuente Pedersen, PA

(57) ABSTRACT

There is described an apparatus for heating or cooling a material to be heated or to be cooled. The apparatus includes: a first compartment for containing the material to be heated or to be cooled; and a second compartment containing a phase change material, wherein the phase change material is either for generating heat to heat the first compartment or absorbing heat to cool the first compartment when undergoing a phase change. There are further described various different activating arrangements for activating a change of phase of the phase change material.

10 Claims, 7 Drawing Sheets

(58) Field of Classification Search
USPC .................................................................. 62/4
See application file for complete search history.

(56) References Cited

U.S. PATENT DOCUMENTS

| | | | |
|---|---|---|---|
| 2,888,208 A | 5/1959 | Fedit | |
| 3,040,991 A | 6/1962 | Fedit | |
| 3,043,524 A | 7/1962 | Boris | |
| 3,258,015 A | 6/1966 | Herbert et al. | |
| 3,289,949 A | 12/1966 | Roth | |
| 3,347,231 A | 10/1967 | Chang | |
| 3,522,806 A | 8/1970 | Szekely | |
| 3,647,143 A | 3/1972 | Gauthier et al. | |
| 3,658,059 A | 4/1972 | Steil | |
| 3,733,010 A | 5/1973 | Riccio | |
| 3,856,185 A | 12/1974 | Riccio | |
| 3,864,326 A | 2/1975 | Babington et al. | |
| 3,913,843 A | 10/1975 | Cambio, Jr. | |
| 3,943,942 A | 3/1976 | Anderson | |
| 4,149,548 A | 4/1979 | Bradshaw | |
| 4,284,089 A | 8/1981 | Ray | |
| 4,299,274 A | 11/1981 | Campbell et al. | |
| 4,299,355 A | 11/1981 | Hakkinen | |
| 4,303,541 A | 12/1981 | Wasel-Nielen et al. | |
| 4,393,884 A | 7/1983 | Jacobs | |
| 4,412,930 A | 11/1983 | Koike et al. | |
| 4,429,835 A | 2/1984 | Brugger et al. | |
| 4,694,841 A | 9/1987 | Esparza | |
| 4,734,097 A * | 3/1988 | Tanabe | A61L 27/16 |
| | | | 264/28 |
| 4,746,067 A | 5/1988 | Svoboda | |
| 4,765,348 A | 8/1988 | Honeycutt | |
| 4,771,795 A | 9/1988 | White et al. | |
| 4,776,353 A | 10/1988 | Lilja et al. | |
| 4,819,665 A | 4/1989 | Roberts et al. | |
| 4,827,950 A | 5/1989 | Banerjee et al. | |
| 4,892,109 A | 1/1990 | Strubel | |
| 4,907,606 A | 3/1990 | Lilja | |
| 4,913,168 A | 4/1990 | Potter et al. | |
| 4,917,119 A | 4/1990 | Potter et al. | |
| 4,917,120 A | 4/1990 | Hill | |
| 4,924,883 A | 5/1990 | Perfetti et al. | |
| 4,938,236 A | 7/1990 | Banerjee et al. | |
| 4,941,483 A | 7/1990 | Ridings et al. | |
| 4,947,874 A | 8/1990 | Brooks et al. | |
| 4,955,399 A * | 9/1990 | Potter | A24F 47/006 |
| | | | 131/359 |
| 5,019,122 A | 5/1991 | Clearman et al. | |
| 5,020,509 A | 6/1991 | Suzuki et al. | |
| 5,040,552 A | 8/1991 | Schleich et al. | |
| 5,042,509 A | 8/1991 | Banerjee et al. | |
| 5,060,667 A | 10/1991 | Strubel | |
| 5,060,671 A | 10/1991 | Counts et al. | |
| 5,076,292 A | 12/1991 | Sensabaugh et al. | |
| 5,080,115 A | 1/1992 | Templeton | |
| 5,093,894 A | 3/1992 | Deevi et al. | |
| 5,095,921 A | 3/1992 | Losee et al. | |
| 5,097,850 A | 3/1992 | Braunshteyn et al. | |
| 5,099,861 A | 3/1992 | Clearman et al. | |
| 5,105,831 A | 4/1992 | Banerjee et al. | |
| 5,119,834 A | 6/1992 | Shannon et al. | |
| 5,133,368 A | 7/1992 | Neumann | |
| 5,143,048 A | 9/1992 | Cheney, III | |
| 5,144,962 A | 9/1992 | Counts et al. | |
| 5,146,934 A | 9/1992 | Deevi et al. | |
| 5,159,940 A | 11/1992 | Hayward et al. | |
| 5,167,242 A | 12/1992 | Turner et al. | |
| 5,179,966 A | 1/1993 | Losee et al. | |
| 5,188,130 A | 2/1993 | Hajaligol et al. | |
| 5,224,498 A | 7/1993 | Deevi | |
| 5,230,715 A | 7/1993 | Iizuna | |
| 5,235,992 A | 8/1993 | Sensabaugh, Jr. | |
| 5,240,012 A * | 8/1993 | Ehrman | A24F 47/004 |
| | | | 131/182 |
| 5,261,424 A | 11/1993 | Sprinkel | |
| 5,269,327 A | 12/1993 | Counts et al. | |
| 5,285,798 A * | 2/1994 | Banerjee | A24B 15/165 |
| | | | 131/194 |
| 5,293,883 A | 3/1994 | Edwards | |
| 5,305,733 A | 4/1994 | Walters | |
| 5,312,046 A | 5/1994 | Knoch et al. | |
| 5,327,915 A | 7/1994 | Porenski et al. | |
| 5,345,951 A | 9/1994 | Serrano et al. | |
| 5,357,984 A | 10/1994 | Farrier et al. | |
| 5,369,723 A | 11/1994 | Counts et al. | |
| 5,396,911 A | 3/1995 | Casey et al. | |
| 5,400,808 A | 3/1995 | Turner et al. | |
| 5,408,574 A | 4/1995 | Deevi et al. | |
| 5,415,186 A | 5/1995 | Casey et al. | |
| 5,443,560 A | 8/1995 | Deevi et al. | |
| 5,454,363 A | 10/1995 | Sata | |
| 5,461,695 A | 10/1995 | Knoch | |
| 5,474,059 A | 12/1995 | Cooper | |
| 5,501,236 A | 3/1996 | Hill et al. | |
| 5,511,538 A | 4/1996 | Haber | |
| 5,517,981 A | 5/1996 | Taub et al. | |
| 5,534,020 A | 7/1996 | Cheney, III et al. | |
| 5,538,020 A | 7/1996 | Farrier | |
| 5,549,906 A | 8/1996 | Santus | |
| 5,564,442 A | 10/1996 | MacDonald et al. | |
| 5,593,792 A | 1/1997 | Farrier et al. | |
| 5,613,505 A | 3/1997 | Campbell et al. | |
| 5,645,749 A | 7/1997 | Wang | |
| 5,649,554 A | 7/1997 | Sprinkel et al. | |
| 5,659,656 A | 8/1997 | Das | |
| 5,687,912 A | 11/1997 | Denyer | |
| 5,699,786 A | 12/1997 | Oshima et al. | |
| 5,711,292 A | 1/1998 | Hammarlund | |
| 5,736,110 A | 4/1998 | Angelillo et al. | |
| 5,778,899 A | 7/1998 | Saito et al. | |
| 5,819,756 A * | 10/1998 | Mielordt | A24F 47/008 |
| | | | 131/330 |
| 5,845,649 A | 12/1998 | Saito et al. | |
| 5,865,186 A | 2/1999 | Volsey | |
| 5,921,233 A | 7/1999 | Gold et al. | |
| 5,935,486 A | 8/1999 | Bell et al. | |
| 5,938,125 A | 8/1999 | Ritsche et al. | |
| 5,984,953 A | 11/1999 | Sabin | |
| 6,000,394 A | 12/1999 | Blaha-Schnabel | |
| 6,041,790 A | 3/2000 | Smith et al. | |
| 6,053,176 A | 4/2000 | Adams et al. | |
| 6,079,405 A | 6/2000 | Justo | |
| 6,085,741 A | 7/2000 | Becker | |
| 6,089,857 A | 7/2000 | Matsuura et al. | |
| 6,113,078 A | 9/2000 | Rock | |
| 6,116,231 A * | 9/2000 | Sabin | A61F 7/03 |
| | | | 126/263.01 |
| 6,129,080 A | 10/2000 | Pitcher et al. | |
| 6,158,676 A | 12/2000 | Hughes | |
| 6,164,287 A | 12/2000 | White | |
| 6,178,963 B1 | 1/2001 | Baik | |
| 6,209,457 B1 | 4/2001 | Kenworthy et al. | |
| 6,223,745 B1 | 5/2001 | Hammarlund et al. | |
| 6,230,703 B1 | 5/2001 | Bono | |
| 6,234,459 B1 | 5/2001 | Rock | |
| 6,244,573 B1 | 6/2001 | Rock | |
| 6,248,257 B1 | 6/2001 | Bell et al. | |
| 6,267,110 B1 | 7/2001 | Tenenboum et al. | |
| 6,283,116 B1 | 9/2001 | Yang | |
| 6,289,889 B1 | 9/2001 | Bell | |
| 6,347,789 B1 | 2/2002 | Rock | |
| 6,427,878 B1 | 8/2002 | Greiner-Perth et al. | |
| 6,595,209 B1 | 7/2003 | Rose et al. | |
| 6,598,607 B2 | 7/2003 | Adiga et al. | |
| 6,644,383 B2 * | 11/2003 | Joseph | B65D 81/3484 |
| | | | 165/46 |
| 6,648,306 B2 | 11/2003 | Rock | |
| 6,669,176 B2 | 12/2003 | Rock | |
| 6,708,846 B1 | 3/2004 | Fuchs et al. | |
| 6,723,115 B1 | 4/2004 | Daly | |
| 6,761,164 B2 | 7/2004 | Amirpour et al. | |
| 6,769,436 B2 | 8/2004 | Horian | |
| 6,799,572 B2 | 10/2004 | Nichols et al. | |
| 6,803,545 B2 | 10/2004 | Blake et al. | |

(56) References Cited

U.S. PATENT DOCUMENTS

| | | | |
|---|---|---|---|
| 6,827,080 B2 * | 12/2004 | Fish | A61F 7/03 126/263.01 |
| 6,886,556 B2 | 5/2005 | Fuchs | |
| 6,953,474 B2 * | 10/2005 | Lu | A61F 7/03 607/108 |
| 6,968,888 B2 | 11/2005 | Kolowich | |
| 7,041,123 B2 | 5/2006 | Stapf et al. | |
| 7,077,130 B2 | 7/2006 | Nichols et al. | |
| 7,081,211 B2 | 7/2006 | Li et al. | |
| 7,088,914 B2 | 8/2006 | Whittle et al. | |
| 7,163,014 B2 | 1/2007 | Nichols et al. | |
| 7,234,459 B2 | 6/2007 | Del Bon | |
| 7,235,187 B2 | 6/2007 | Li et al. | |
| 7,290,549 B2 | 11/2007 | Banerjee et al. | |
| 7,303,328 B2 | 12/2007 | Faraldi et al. | |
| 7,335,186 B2 | 2/2008 | O'Neil | |
| 7,373,938 B2 | 5/2008 | Nichols et al. | |
| 7,434,584 B2 | 10/2008 | Steinberg | |
| 7,540,286 B2 | 6/2009 | Cross et al. | |
| 7,548,374 B2 | 6/2009 | Raymond et al. | |
| 7,581,540 B2 | 9/2009 | Hale et al. | |
| 7,581,718 B1 | 9/2009 | Chang | |
| 7,585,493 B2 | 9/2009 | Hale et al. | |
| 7,645,442 B2 | 1/2010 | Hale et al. | |
| 7,665,461 B2 | 2/2010 | Zierenberg et al. | |
| 7,832,397 B2 | 11/2010 | Lipowicz | |
| 7,834,295 B2 | 11/2010 | Sharma et al. | |
| 7,987,846 B2 | 8/2011 | Hale et al. | |
| 8,118,021 B2 | 2/2012 | Cho | |
| 8,156,944 B2 | 4/2012 | Han | |
| 8,342,184 B2 | 1/2013 | Inagaki et al. | |
| 8,365,742 B2 | 2/2013 | Hon | |
| 8,375,957 B2 | 2/2013 | Hon | |
| 8,899,238 B2 * | 12/2014 | Robinson | A24F 47/008 131/200 |
| 9,693,587 B2 * | 7/2017 | Plojoux | A61M 15/06 |
| 2001/0042927 A1 | 11/2001 | Rock | |
| 2001/0054421 A1 | 12/2001 | Jaser et al. | |
| 2002/0043260 A1 | 4/2002 | Layer et al. | |
| 2002/0078951 A1 | 6/2002 | Nichols et al. | |
| 2002/0078955 A1 | 6/2002 | Nichols et al. | |
| 2002/0089072 A1 | 7/2002 | Rock | |
| 2002/0121624 A1 | 9/2002 | Usui | |
| 2003/0052196 A1 | 3/2003 | Fuchs | |
| 2003/0097164 A1 | 5/2003 | Stapf et al. | |
| 2003/0101984 A1 | 6/2003 | Li | |
| 2003/0105192 A1 | 6/2003 | Li et al. | |
| 2003/0106551 A1 | 6/2003 | Sprinkel, Jr. et al. | |
| 2003/0111637 A1 | 6/2003 | Li et al. | |
| 2003/0159702 A1 | 8/2003 | Lindell et al. | |
| 2003/0209240 A1 | 11/2003 | Hale et al. | |
| 2003/0217750 A1 | 11/2003 | Amirpour et al. | |
| 2003/0226837 A1 | 12/2003 | Blake et al. | |
| 2004/0065314 A1 | 4/2004 | Layer et al. | |
| 2004/0068222 A1 | 4/2004 | Brian | |
| 2004/0083755 A1 | 5/2004 | Kolowich | |
| 2004/0177849 A1 | 9/2004 | Del Bon | |
| 2004/0234699 A1 | 11/2004 | Hale et al. | |
| 2004/0234914 A1 | 11/2004 | Hale et al. | |
| 2004/0234916 A1 | 11/2004 | Hale et al. | |
| 2004/0255941 A1 | 12/2004 | Nichols et al. | |
| 2004/0261782 A1 | 12/2004 | Furumichi et al. | |
| 2005/0007870 A1 | 1/2005 | Faraldi et al. | |
| 2005/0016549 A1 * | 1/2005 | Banerjee | A24B 15/16 131/194 |
| 2005/0045193 A1 | 3/2005 | Yang | |
| 2005/0063686 A1 | 3/2005 | Whittle et al. | |
| 2005/0079166 A1 | 4/2005 | Damani et al. | |
| 2005/0133029 A1 | 6/2005 | Nichols et al. | |
| 2005/0196345 A1 | 9/2005 | Diederichs et al. | |
| 2005/0236006 A1 | 10/2005 | Cowan | |
| 2006/0027233 A1 | 2/2006 | Zierenberg et al. | |
| 2006/0032501 A1 | 2/2006 | Hale et al. | |
| 2006/0102175 A1 | 5/2006 | Nelson | |
| 2006/0118128 A1 | 6/2006 | Hoffman | |
| 2006/0137681 A1 | 6/2006 | Von Hollen et al. | |
| 2006/0191546 A1 | 8/2006 | Takano | |
| 2006/0196885 A1 | 9/2006 | Leach et al. | |
| 2007/0023043 A1 | 2/2007 | Von Hollen et al. | |
| 2007/0028916 A1 | 2/2007 | Hale et al. | |
| 2007/0031340 A1 | 2/2007 | Hale et al. | |
| 2007/0102533 A1 | 5/2007 | Rosell et al. | |
| 2007/0125362 A1 | 6/2007 | Ford et al. | |
| 2007/0131219 A1 | 6/2007 | Ford et al. | |
| 2007/0138207 A1 | 6/2007 | Bonney et al. | |
| 2007/0175476 A1 | 8/2007 | Lipowicz | |
| 2007/0204864 A1 | 9/2007 | Grychowski et al. | |
| 2007/0222112 A1 | 9/2007 | Christ et al. | |
| 2007/0283972 A1 | 12/2007 | Monsees et al. | |
| 2007/0289720 A1 | 12/2007 | Sunol et al. | |
| 2008/0038363 A1 | 2/2008 | Zaffaroni et al. | |
| 2008/0149118 A1 | 6/2008 | Oglesby et al. | |
| 2008/0156326 A1 | 7/2008 | Belcastro et al. | |
| 2008/0216828 A1 | 9/2008 | Wensley et al. | |
| 2008/0241255 A1 | 10/2008 | Rose et al. | |
| 2008/0257367 A1 | 10/2008 | Paterno et al. | |
| 2008/0276947 A1 | 11/2008 | Martzel | |
| 2008/0312674 A1 | 12/2008 | Chen et al. | |
| 2009/0015717 A1 | 1/2009 | Arnao et al. | |
| 2009/0065011 A1 * | 3/2009 | Maeder | A24F 47/006 131/194 |
| 2009/0071477 A1 | 3/2009 | Hale et al. | |
| 2009/0078711 A1 | 3/2009 | Farone et al. | |
| 2009/0090349 A1 | 4/2009 | Donovan | |
| 2009/0090351 A1 | 4/2009 | Sunol et al. | |
| 2009/0095287 A1 | 4/2009 | Emarlou | |
| 2009/0107492 A1 | 4/2009 | Ooida | |
| 2009/0114215 A1 | 5/2009 | Boeck et al. | |
| 2009/0151717 A1 | 6/2009 | Bowen et al. | |
| 2009/0162294 A1 | 6/2009 | Werner | |
| 2009/0180968 A1 | 7/2009 | Hale et al. | |
| 2009/0199843 A1 | 8/2009 | Farone et al. | |
| 2009/0217923 A1 | 9/2009 | Boehm et al. | |
| 2009/0230117 A1 | 9/2009 | Fernando et al. | |
| 2009/0260641 A1 | 10/2009 | Monsees et al. | |
| 2009/0260642 A1 | 10/2009 | Monsees et al. | |
| 2009/0280043 A1 | 11/2009 | Ferguson | |
| 2009/0301363 A1 | 12/2009 | Damani et al. | |
| 2009/0301471 A1 | 12/2009 | Stirzel | |
| 2009/0302019 A1 | 12/2009 | Selenski et al. | |
| 2010/0006092 A1 | 1/2010 | Hale et al. | |
| 2010/0025023 A1 | 2/2010 | Schmidt et al. | |
| 2010/0031968 A1 | 2/2010 | Sheikh et al. | |
| 2010/0043809 A1 | 2/2010 | Magnon | |
| 2010/0065052 A1 | 3/2010 | Sharma et al. | |
| 2010/0068154 A1 | 3/2010 | Sharma et al. | |
| 2010/0089381 A1 | 4/2010 | Bolmer et al. | |
| 2010/0181387 A1 | 7/2010 | Zaffaroni et al. | |
| 2010/0236546 A1 | 9/2010 | Yamada et al. | |
| 2010/0242974 A1 | 9/2010 | Pan | |
| 2010/0258585 A1 | 10/2010 | Jamison | |
| 2010/0300467 A1 | 12/2010 | Kuistila et al. | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0030671 A1 | 2/2011 | Ferguson et al. | |
| 2011/0192408 A1 | 8/2011 | Inagaki et al. | |
| 2011/0283458 A1 | 11/2011 | Gillette et al. | |
| 2011/0290266 A1 | 12/2011 | Marcel | |
| 2012/0006342 A1 | 1/2012 | Rose et al. | |
| 2012/0006343 A1 | 1/2012 | Renaud et al. | |
| 2012/0132196 A1 | 5/2012 | Vladyslavovych | |
| 2012/0145189 A1 | 6/2012 | Knopow et al. | |
| 2013/0061861 A1 | 3/2013 | Hearn | |
| 2014/0338680 A1 | 11/2014 | Abramov et al. | |
| 2015/0142088 A1 | 5/2015 | Riva | |
| 2015/0223520 A1 * | 8/2015 | Phillips | A61M 15/06 131/328 |
| 2016/0146506 A1 * | 5/2016 | Brereton | A24F 47/006 126/263.07 |
| 2016/0168438 A1 | 6/2016 | Harding et al. | |
| 2017/0196262 A1 | 7/2017 | Brereton | |
| 2017/0231281 A1 | 8/2017 | Hatton | |
| 2017/0303585 A1 * | 10/2017 | Florack | A24F 47/006 |

(56) References Cited

U.S. PATENT DOCUMENTS

| | | | |
|---|---|---|---|
| 2017/0332700 | A1 | 11/2017 | Plews |
| 2017/0340008 | A1* | 11/2017 | Sebastian ............... A24D 1/025 |
| 2019/0000142 | A1* | 1/2019 | Lavanchy ............ A24F 47/006 |
| 2019/0014820 | A1* | 1/2019 | Malgat ................. A24F 47/006 |

FOREIGN PATENT DOCUMENTS

| | | | |
|---|---|---|---|
| AT | 321190 | | 3/1975 |
| AT | 321191 | | 3/1975 |
| AU | 2002364521 | | 6/2003 |
| CA | 2146954 | | 10/1996 |
| CA | 2414161 | | 1/2002 |
| CA | 2414191 | | 1/2002 |
| CA | 2520759 | | 10/2004 |
| CA | 2492255 | | 7/2006 |
| CA | 2668465 | | 5/2009 |
| CA | 2712412 | | 12/2009 |
| CA | 2712412 | A1 * | 12/2009 ........... A24F 47/006 |
| CA | 2641869 | | 6/2010 |
| CH | 513656 | | 10/1971 |
| CH | 698603 | | 9/2009 |
| CN | 1038085 | | 12/1989 |
| CN | 1043076 | | 6/1990 |
| CN | 1045691 | | 10/1990 |
| CN | 1059649 | | 3/1992 |
| CN | 1123000 | | 5/1996 |
| CN | 1123001 | | 5/1996 |
| CN | 1126426 | | 7/1996 |
| CN | 1158757 | | 9/1997 |
| CN | 1287890 | | 3/2001 |
| CN | 1293591 | | 5/2001 |
| CN | 1293596 | | 5/2001 |
| CN | 102212340 | | 10/2001 |
| CN | 1578895 | A | 2/2005 |
| CN | 101500443 | | 8/2009 |
| CN | 101516425 | | 8/2009 |
| CN | 102131411 | A | 7/2011 |
| CN | 102499466 | | 6/2012 |
| CN | 102604599 | | 7/2012 |
| CN | 202351223 | | 7/2012 |
| DE | 1100884 | | 3/1961 |
| DE | 1425872 | | 11/1968 |
| DE | 1290499 | | 3/1969 |
| DE | 1813993 | | 6/1970 |
| DE | 1425871 | | 10/1970 |
| DE | 2315789 | | 10/1973 |
| DE | 4105370 | | 8/1992 |
| DE | 4307144 | | 1/1995 |
| DE | 29509286 | | 10/1995 |
| DE | 4420366 | | 12/1995 |
| DE | 29700307 | | 5/1997 |
| DE | 19854007 | | 5/2000 |
| DE | 19854009 | | 5/2000 |
| DE | 10058642 | | 6/2001 |
| DE | 10007521 | | 8/2001 |
| DE | 10064288 | | 8/2001 |
| DE | 10164587 | | 7/2003 |
| DE | 102005024803 | | 6/2006 |
| DE | 102005023278 | A1 | 11/2006 |
| DE | 202006013439 | | 11/2006 |
| DE | 102005056885 | | 5/2007 |
| DE | 102006041544 | | 8/2007 |
| DE | 102006041042 | | 3/2008 |
| DE | 102006047146 | | 4/2008 |
| DE | 102007011120 | | 9/2008 |
| DE | 102008034509 | | 4/2009 |
| DE | 102008013303 | | 9/2009 |
| DE | 202009010400 | | 12/2009 |
| DE | 102008038121 | | 2/2010 |
| DE | 202010011436 | | 12/2010 |
| DE | 102010046482 | | 3/2012 |
| DE | 102013002555 | | 6/2014 |
| DK | 114399 | | 6/1969 |
| DK | 488488 | | 3/1989 |
| DK | 540774 | | 7/1995 |
| DK | 540775 | | 8/1997 |
| EP | 0033668 | | 8/1981 |
| EP | 33668 | | 8/1981 |
| EP | 0076897 | | 4/1983 |
| EP | 0149997 | | 7/1985 |
| EP | 0194257 | | 9/1986 |
| EP | 0309227 | A2 | 3/1989 |
| EP | 0 371 285 | A2 | 6/1990 |
| EP | 0371285 | | 6/1990 |
| EP | 0430559 | | 12/1991 |
| EP | 0520231 | | 12/1991 |
| EP | 0491 952 | A1 | 7/1992 |
| EP | 0354661 | | 4/1997 |
| EP | 540775 | | 7/1997 |
| EP | 0824927 | | 2/1998 |
| EP | 653218 | | 9/1998 |
| EP | 1111191 | | 6/2001 |
| EP | 1128741 | | 9/2001 |
| EP | 1128742 | | 9/2001 |
| EP | 1128743 | | 9/2001 |
| EP | 1148905 | | 10/2001 |
| EP | 2003997 | | 10/2001 |
| EP | 1203189 | | 5/2002 |
| EP | 1217320 | | 6/2002 |
| EP | 1298993 | | 4/2003 |
| EP | 1299499 | | 4/2003 |
| EP | 1299500 | | 4/2003 |
| EP | 1301152 | | 4/2003 |
| EP | 1349601 | | 10/2003 |
| EP | 1390112 | | 2/2004 |
| EP | 1409051 | | 4/2004 |
| EP | 1439876 | | 7/2004 |
| EP | 1490452 | | 12/2004 |
| EP | 1506792 | | 2/2005 |
| EP | 1609376 | A1 | 12/2005 |
| EP | 1625334 | | 2/2006 |
| EP | 1625335 | | 2/2006 |
| EP | 1625336 | | 2/2006 |
| EP | 1536703 | | 9/2006 |
| EP | 1702639 | | 9/2006 |
| EP | 1749548 | | 2/2007 |
| EP | 1867357 | | 12/2007 |
| EP | 1891867 | | 2/2008 |
| EP | 1996880 | | 12/2008 |
| EP | 2044967 | | 4/2009 |
| EP | 2277398 | | 7/2009 |
| EP | 2083642 | | 8/2009 |
| EP | 2138058 | | 12/2009 |
| EP | 2138059 | | 12/2009 |
| EP | 2179229 | | 4/2010 |
| EP | 2191735 | | 6/2010 |
| EP | 2227973 | | 9/2010 |
| EP | 2234508 | | 10/2010 |
| EP | 2241203 | | 10/2010 |
| EP | 2138057 | | 11/2010 |
| EP | 2246086 | | 11/2010 |
| EP | 2249669 | | 11/2010 |
| EP | 2257195 | | 12/2010 |
| EP | 2303043 | | 4/2011 |
| EP | 2368449 | | 9/2011 |
| EP | 2408494 | | 1/2012 |
| EP | 2523752 | | 11/2012 |
| EP | 2542131 | | 1/2013 |
| ES | 262308 | | 6/1982 |
| FR | 1418189 | | 11/1965 |
| FR | 2573985 | | 6/1986 |
| FR | 2604093 | | 3/1988 |
| FR | 2700697 | | 7/1994 |
| FR | 2730166 | | 8/1996 |
| FR | 2818152 | | 6/2002 |
| FR | 2842791 | | 1/2005 |
| FR | 2873584 | | 11/2006 |
| GB | 910166 | | 11/1962 |
| GB | 922310 | | 3/1963 |
| GB | 958867 | | 5/1964 |
| GB | 1104214 | | 2/1968 |
| GB | 1227333 | | 4/1971 |
| GB | 1379688 | | 1/1975 |
| GB | 1431334 | | 4/1976 |

(56) References Cited

FOREIGN PATENT DOCUMENTS

| | | |
|---|---|---|
| GB | 2323033 | 9/1998 |
| GB | 2342874 | 4/2000 |
| GB | 2388040 | 11/2003 |
| GB | 2412326 | 9/2005 |
| GB | 2412876 | 10/2005 |
| GB | 2448478 | 10/2008 |
| GB | 2487851 | 8/2012 |
| IE | 63083 | 3/1995 |
| IT | 1289590 | 10/1998 |
| JP | 49061986 | 6/1974 |
| JP | 50096908 | 8/1975 |
| JP | 53014173 | 2/1978 |
| JP | 55094260 | 7/1980 |
| JP | 57110260 | 7/1982 |
| JP | 57177769 | 11/1982 |
| JP | 62205184 | 9/1987 |
| JP | S63-60322 | 3/1988 |
| JP | 63153666 | 6/1988 |
| JP | 01191674 | 8/1989 |
| JP | H01191674 | 8/1989 |
| JP | 02092986 | 4/1990 |
| JP | 02127493 | 5/1990 |
| JP | 02190171 | 7/1990 |
| JP | 03041185 | 2/1991 |
| JP | 03112478 | 5/1991 |
| JP | 6-2164 | 1/1994 |
| JP | 2519658 | 7/1996 |
| JP | 08228751 | 9/1996 |
| JP | 3053426 | 10/1998 |
| JP | 11178562 | 7/1999 |
| JP | 3016586 | 3/2000 |
| JP | 2000119643 | 4/2000 |
| JP | 3078033 | 8/2000 |
| JP | 3118462 | 12/2000 |
| JP | 3118463 | 12/2000 |
| JP | 2001063776 | 3/2001 |
| JP | 2002253593 | 9/2002 |
| JP | 2002529111 | 9/2002 |
| JP | 2002336290 | 11/2002 |
| JP | 2003034785 | 2/2003 |
| JP | 2004504580 | 2/2004 |
| JP | 2005516647 | 6/2005 |
| JP | 2006219557 | 8/2006 |
| JP | 2007516015 | 6/2007 |
| JP | 2007522900 | 8/2007 |
| JP | 2008509907 | 4/2008 |
| JP | 2010526553 | 8/2010 |
| JP | 2011525366 | 9/2011 |
| RU | 2066337 C1 | 9/1996 |
| RU | 2098446 C1 | 12/1997 |
| RU | 2285028 C1 | 10/2006 |
| SE | 502503 | 10/2006 |
| WO | WO8601730 | 3/1986 |
| WO | WO9527411 | 10/1995 |
| WO | WO9805906 | 2/1998 |
| WO | WO9835552 | 8/1998 |
| WO | WO9914402 | 3/1999 |
| WO | WO9947273 | 9/1999 |
| WO | WO9947806 | 9/1999 |
| WO | WO9013326 | 11/1999 |
| WO | WO0028842 | 5/2000 |
| WO | WO0028843 | 5/2000 |
| WO | WO0104548 | 1/2001 |
| WO | WO0140717 | 6/2001 |
| WO | WO0163183 | 8/2001 |
| WO | WO0205620 | 1/2002 |
| WO | WO0205640 | 1/2002 |
| WO | WO0206421 | 1/2002 |
| WO | WO0207656 | 1/2002 |
| WO | WO0224262 | 3/2002 |
| WO | WO02051466 | 7/2002 |
| WO | WO02096532 | 12/2002 |
| WO | WO03037412 | 5/2003 |
| WO | WO03049792 | 6/2003 |
| WO | WO083007 | 10/2003 |
| WO | WO 2004089126 | 10/2004 |
| WO | WO2004098324 | 11/2004 |
| WO | WO2004104491 | 12/2004 |
| WO | WO2004104492 | 12/2004 |
| WO | WO2004104493 | 12/2004 |
| WO | WO2006022714 | 3/2006 |
| WO | WO2007054167 | 5/2007 |
| WO | WO2007078273 | 7/2007 |
| WO | WO2007090594 | 8/2007 |
| WO | WO2007098337 | 8/2007 |
| WO | WO2007116915 | 10/2007 |
| WO | WO2008015441 | 2/2008 |
| WO | WO 2008/051909 A1 | 5/2008 |
| WO | WO2008069883 | 6/2008 |
| WO | WO2008151777 | 12/2008 |
| WO | WO2009006521 | 1/2009 |
| WO | WO2009042955 | 4/2009 |
| WO | WO2009079641 | 6/2009 |
| WO | WO2009092862 | 7/2009 |
| WO | WO2009118085 | 10/2009 |
| WO | WO2009152651 | 12/2009 |
| WO | WO2009155957 | 12/2009 |
| WO | WO2009156181 | 12/2009 |
| WO | WO2010017586 | 2/2010 |
| WO | WO2010047389 | 4/2010 |
| WO | WO2010053467 | 5/2010 |
| WO | WO2010060537 | 6/2010 |
| WO | WO2010102832 | 9/2010 |
| WO | WO2010107613 | 9/2010 |
| WO | WO2011045609 | 4/2011 |
| WO | WO2011088132 | 7/2011 |
| WO | WO2011101164 | 8/2011 |
| WO | WO201117580 | 9/2011 |
| WO | WO2011109304 | 9/2011 |
| WO | WO2012014490 | 2/2012 |
| WO | WO2012054973 | 5/2012 |
| WO | WO2012078865 | 6/2012 |
| WO | WO2012100430 | 8/2012 |
| WO | WO 2013/113612 | 8/2013 |
| WO | WO 2014/045025 | 3/2014 |

OTHER PUBLICATIONS

Japanese Office Action, Application No. 2016-575543, dated Dec. 4, 2018, 17 pages.
Application and File History for U.S. Appl. No. 16/220,516, filed Dec. 14, 2018, Inventor: Harding.
Journal of Zhejiang, University of Technology, vol. 34, No. 6, Zhang Xuemei et al., Experimental Researches for Improving the Heat Storage Performance of Sodium Acetate Trihydrate, p. 689, 2, Dec. 31, 2006.
Journal of Central China Normal University, vol. 21, No. 3; Ruan Deshui, et al., Studies on the Sodium Acetate Trihydrate for Latent Heat Storage; 393-394, Table 1; Sep. 30, 1987.
Jiangsu Chemical Industry, No. 1; Zhang Wenzhao, et al., Development of Sodium Acetate Trihydrate as Heat Storage Material, pp. 31-33; Dec. 31, 1992.
Journal of Central China Normal University, vol. 23, No. 1; Ruan Deshui, et al., The Effect of Additives on the Linear Crystallization Velocity of Sodium Acetate Trihydrate, pp. 57-60, Mar. 31, 1989.
Translation of Chinese Office Action, Application No. 201480037847.5, dated Jan. 2, 2019. 12 pages.
International Search Report for corresponding International Application No. PCT/EP2015/064595 dated Jan. 5, 2016; 6 pages.
Written Opinion of the International Searching Authority for corresponding International Application No. PCT/EP2015/064595 dated Jan. 5, 2016; 11 pages.
International Preliminary Report on Patentability for corresponding International Application No. PCT/EP2015/064595 dated Oct. 25, 2016; 20 pages.
Written Opinion of the International Preliminary Examining Authority for corresponding International Application No. PCT/EP2015/064595 dated Jun. 13, 2016, 8 pages.
International Search Report for corresponding International Application No. PCT/EP2014/063785 dated Oct. 30, 2014; 3 pages.

(56) References Cited

OTHER PUBLICATIONS

Written Opinion of the International Searching Authority for corresponding International Application No. PCT/EP2014/063785 dated Oct. 30, 2014; 6 pages.
International Preliminary Report on Patentability for corresponding International Application No. PCT/EP2014/063785 completed on Jun. 1, 2015; 12 pages.
International Search Report and Written Opinion for International Application No. PCT/EP2014/064365 dated Oct. 7, 2014.
Application and File History for U.S. Appl. No. 14/899,629, filed Dec. 18, 2015, inventors Brereton et al.
Application and File History for U.S. Appl. No. 14/428,344, filed Mar. 13, 2015, inventors Phillipset al.
Application and File History for U.S. Appl. No. 14/902,663, filed Jan. 4, 2016, inventors Harding et al.
Russian Office Action, for Russian Application No. 2016103729, dated Apr. 12, 2017, 15 pages.
Chinese Office Action, Application No. 201480037049.2, dated May 9, 2017, 10 pages, (28 pages with translation).
Japanese Office Action, Application No. 2016-522550, dated Jul. 4, 2017, 4 pages (7 pages with translation)
Japanese Decision to Grant a Patent, Application No. 2016-522550, dated Nov. 14, 2017, 3 pages (6 pages with translation).
Japanese Office Action, Application No. 2016-522550, dated Jan. 31, 2017, 4 pages (7 pages with translation).
Chinese Office Action, Application No. 2013800472843, dated Nov. 13, 2017, 4 pages (13 pages with translation).
Japanese Office Action, Application No. 2017-017842, dated Dec. 26, 2017, 3 pages (6 pages with translation).
Honcova, Pavia, "Suppressing supercooling in magnesium nitrate hexahydrate and evaluating corrosoin of aluminium alloy container for latent heat storage application", Published Mar. 30, 2017, Journal of Thermal Analysis and Calorimetry, Volurnne 129, pp. 1573-1581. (Year: 2017).
Japanese Office Action, Application No. 2016-522646, dated Dec. 15, 2016, 6 pages.
UKIPO Search Report dated Jan. 17, 2013 for UK Patent Application No. GB1216621.1 filed Sep. 18, 2012.
International Search Report and Written Opinion dated Jun. 30, 2014 for International Patent Application No. PCT/GB2013/052433 filed Sep. 18, 2013.
International Preliminary Report on Patentability dated Mar. 24, 2015 for International Patent Application No. PCT/GB2013/052433 filed Sep. 18, 2013.
International Search Report and Written Opinion dated Dec. 9, 2013 for International Patent Application No. PCT/EP2013/068797 filed Sep. 11, 2013.
International Preliminary Report on Patentability dated Mar. 31, 2015 for International Patent Application No. PCT/EP2013/068797 filed Sep. 11, 2013.

\* cited by examiner

APPARATUS FOR HEATING OR COOLING A MATERIAL CONTAINED THEREIN

CROSS-REFERENCE TO RELATED APPLICATIONS

The present application is a National Phase entry of PCT Application No. PCT/EP2015/064595, filed on 26 Jun. 2015, which claims priority to GB Patent Application No. 1500582.0, filed on 14 Jan. 2015, and also claims priority to PCT/EP2014/063785, filed on 27 Jun. 2014, which are hereby fully incorporated herein by reference.

TECHNICAL FIELD

The present disclosure relates to apparatus for heating or cooling a material.

BACKGROUND

Various containers or packaging are known that comprise an internal heat source that can be activated in order to heat material contained in the container, or, that comprise an internal heat sink that can be activated in order to cool material contained in the container.

For example, food or drink containers or packaging may comprise such a heat source or a heat sink so that food or drink contained in the containers can be heated or cooled when a user is outdoors and so does not have access to home appliances, for example, cookers, fridges and the like that are normally used for heating or cooling food or drink at home.

Smoking articles such as cigarettes, cigars and the like burn tobacco during use to create tobacco smoke. Attempts have been made to provide alternatives to these smoking articles by creating products that release compounds without actually combusting and hence which do not create smoke. Examples of such products are so-called "Tobacco Heating Devices", "Tobacco Heating Products" or "Heat not Burn" devices which release compounds by heating, but not burning, aerosol generating material. The aerosol generating material may be for example tobacco or other non-tobacco products, which may or may not contain nicotine. In such products, a heat source is required that can be activated to heat the aerosol generating material on demand in a reliable and consistent way.

SUMMARY

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising a phase change activating agent and a barrier that separates the phase change activating agent from the phase change material, wherein, operating the activating arrangement causes the barrier to rupture so that the phase change activating agent can contact the phase change material in order to activate a change of phase of the phase change material and wherein the barrier is configured to re-seal after being ruptured.

In accordance with some embodiments described herein, there is also provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising one or more capsules contained in the phase change material, each of the one or more capsules encapsulating a phase change activating agent and wherein at least some of the one or more of the capsules are rupturable if a force is applied thereto in order to expose the phase change activating agent to the phase change material so as to activate a change of phase of the phase change material.

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising an electric charge and/or current generator for generating and exposing the phase change material to an electric charge and/or current in order to activate a change of phase of the phase change material.

In accordance with some embodiments described herein, there is provided an apparatus for heating or cooling a material to be heated or to be cooled, the apparatus comprising: a first compartment for containing the material to be heated or to be cooled; a second compartment containing a liquid phase change material, wherein the phase change material is either for generating heat to heat the first compartment or absorbing heat to cool the first compartment when undergoing a phase change from a liquid phase to a solid phase; and an activating arrangement comprising means for generating shearing in the liquid phase change material to induce a phase change of the liquid phase change material.

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change from a liquid phase to a solid phase; and an activating arrangement comprising a housing containing an activating agent for inducing a phase change of the phase change material, wherein the housing is configurable in a closed configuration and in an open configuration, wherein, when the housing is in the closed configuration the activating agent is unable to contact the phase change material and when the housing is in the open configuration the activating agent is able to contact the phase change material, wherein at least one component of the activating arrangement is moveable between first and second positions to configure the housing in the first and second configurations.

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising means for causing localized cooling in one or more regions of the phase change material in order to activate a change of phase of the phase change material.

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising means for causing localized cooling in one or more regions of the phase change material in order to activate a change of phase of the phase change material.

In accordance with some embodiments described herein, there is provided an apparatus for heating or cooling a material to be heated or to be cooled, the apparatus comprising: a first compartment for containing the material to be heated or to be cooled; a second compartment containing a phase change material, wherein the phase change material is either for generating heat to heat the first compartment or absorbing heat to cool the first compartment when undergoing a phase change; and an activating arrangement comprising means for generating vibrations in the phase change material in order to activate a change of phase of the phase change material.

In accordance with some embodiments described herein, there is provided an apparatus for heating or cooling a material to be heated or to be cooled, the apparatus comprising: a first compartment for containing the material to be heated or to be cooled; a second compartment containing a liquid phase change material, wherein the phase change material is either for generating heat to heat the first compartment or absorbing heat to cool the first compartment when undergoing a phase change from a liquid phase to a solid phase; and an activating arrangement comprising a member that can be extended into liquid phase change material in the second compartment and oscillated to initiate the phase change of the phase change material.

BRIEF DESCRIPTION OF THE DRAWINGS

Embodiments of the disclosure will now be described, by way of example only, with reference to the accompanying drawings, in which.

DETAILED DESCRIPTION

As used herein, the term "aerosol generating material" includes materials that provide volatilized components upon heating. "Aerosol generating material" includes any tobacco-containing material and may, for example, include one or more of tobacco, tobacco derivatives including tobacco extracts, expanded tobacco, reconstituted tobacco or tobacco substitutes. "Aerosol generating material" also may include other, non-tobacco, products, including for example flavorants, which, depending on the product, may or may not contain nicotine.

Referring first to FIGS. 1 to 5, there is shown an example of an apparatus 1 arranged to heat aerosol generating material to volatize at least one component of the aerosol generating material. The apparatus 1 is a so-called "Tobacco Heating Product" (THP) apparatus 1.

Figure 3:
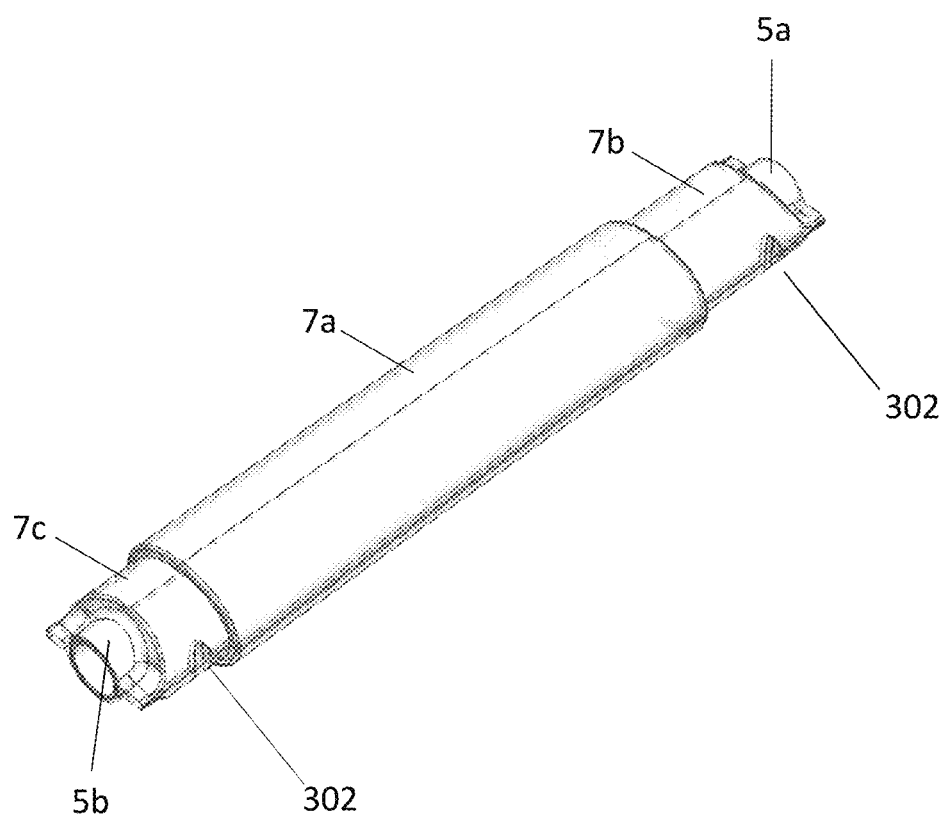
FIG. 3 shows a perspective view of some of the components of the apparatus of FIG. 1.

The apparatus 1 in this example is generally elongate and comprises an outer housing 3 and an inner tube 5. The outer housing 3 comprises an outer tube 7, a mouthpiece 9 and an end cap 11. As best seen in FIG. 3, the outer tube 7 comprises an elongate central section 7a and front 7b and back 7c sections arranged at either end of the central section 7a. The front section 7b and the back section 7c are both slightly narrower than is the central section 7a and are configured so that the mouthpiece 9 can be fitted over the front section 7b and so that the end cap 11 can be fitted over the back section 7c to complete the outer housing 3. The front section 7b and the back section 7c comprise one or more notches 302 which engage with complimentary shaped formations (not shown) suitably positioned on the inside of the mouth piece 9 and end cap 11 respectively to help retain those components in place.

The inner tube 5 is arranged generally concentrically and coaxially inside the outer tube 7. As is best seen in FIG. 3, the inner tube 5 comprises a front end 5a and a back end 5b which extend a small distance out of the front 7b and back 7c sections of the outer tube 7 respectively. The front 7b and back 7c sections of the outer tube 7 are sealed, in any suitable way, for example, by heat sealing, against the outer surface of the inner tube 5 in the region of the front end 5a and back end 5b of the inner tube 5. In this way, the outer tube 7 is closed at both ends whereas the inner tube 5 is open at both ends.

The apparatus 1 may comprise any suitable material or materials, for example, the inner tube 5, the outer tube 7, the mouthpiece 9 and the end cap 11 may each comprise any suitable plastic or metal materials. The mouthpiece 9 (or at least the tip of the mouthpiece 9) may comprise a material that feels comfortable to the lips, for example, silicon rubber.

Figure 1:
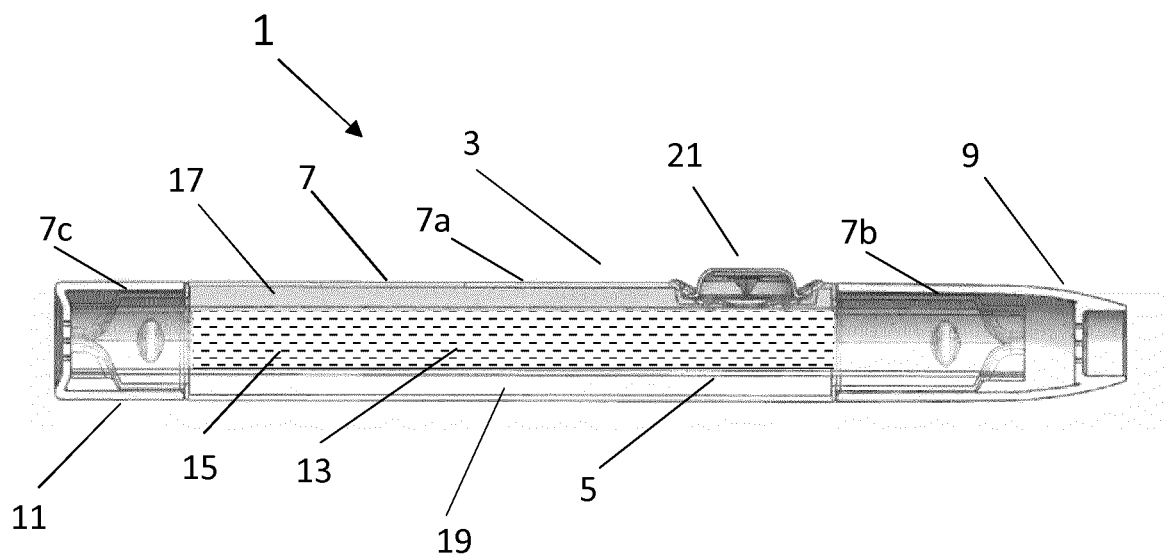
FIG. 1 shows a cross-sectional side view of an example of an apparatus for heating an aerosol generating material.
Figure 2:
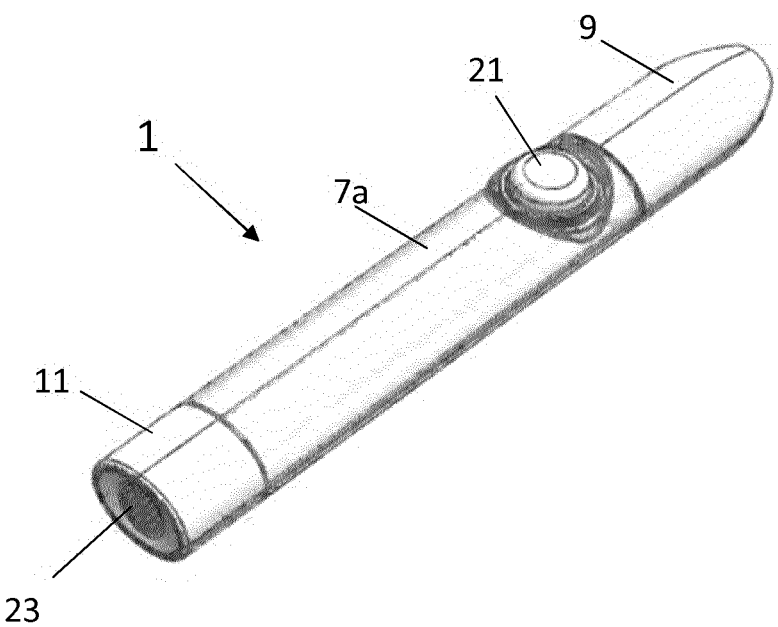
FIG. 2 shows perspective view of the apparatus of FIG. 1.

Referring particularly to the cross-sectional view of FIG. 1, the interior of inner tube 5 acts as a heating chamber 13 for containing an aerosol generating material 15 (illustrated as dashes) to be heated and volatized. The heating chamber 13 is in fluid flow communication with the mouthpiece 9 and the end cap 11.

A generally annular region defined by the outer tube 7 and the inner tube 5 acts as a heat source chamber 17 that contains a heat source material 19 that can be activated to generate heat in order to heat the heating chamber 13 and consequently the aerosol generating material 15 contained in the heating chamber 13.

The heat source material 19 is a phase change material (PCM) which emits heat when activated or induced to undergo a phase change.

In some examples, the heat source material is a liquid material that generates heat when undergoing a phase change to the solid (e.g. crystalline) phase.

In some examples, the heat source material 19 is a hydrated salt PCM. Suitable hydrated salts include sodium acetate trihydrate, sodium hydroxide monohydrate, barium hydroxide octahydrate, magnesium nitrate hexahydrate and magnesium chloride hexahydrate. Sodium acetate trihydrate, for example, is stable at room temperature and is non-hazardous. The phase change of sodium acetate trihydrate from liquid to solid can also be reliably and quickly initiated in a variety of ways.

In the example of FIGS. 1 to 5, the device 1 comprises an activating arrangement 21 (but for clarity not shown in FIG. 3) positioned on the exterior of the outer tube 7 which can be manually operated by a user of the device 1 to induce or activate a phase change of the phase change material 19. Accordingly, in use, when a user operates the activating arrangement 21 to induce a phase change of the phase change material 19, heat released by the phase change material 19, as it undergoes its phase change, heats the aerosol generating material 15 contained in the heating chamber 13. This heat volatizes the aerosol generating material 15 so as to generate aerosol and/or a gas or vapor but without causing aerosol generating material 15 to combust or undergo pyrolysis.

As the user inhales on the mouth piece 9, air is drawn into the heating chamber 13 through one or more air inlets 23 formed in the end cap 11 and a combination of the drawn air and aerosol and/or gas or vapor passes through the heating chamber 13 and enters the mouthpiece 9 for inhalation by the user.

Figure 4:
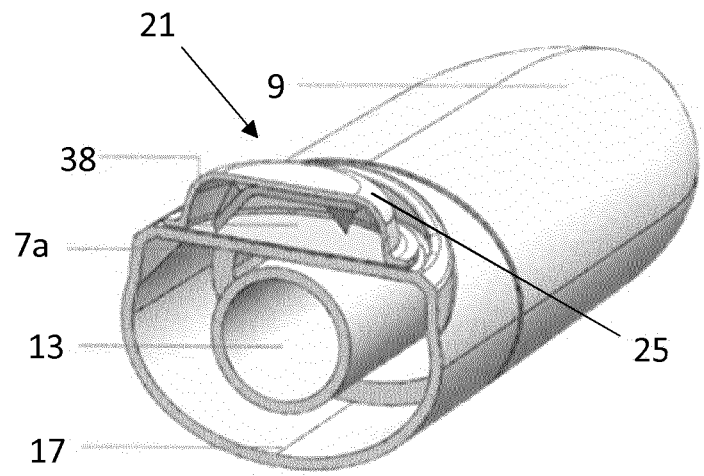
FIG. 4 shows a perspective cut away view of some of the components of the apparatus of FIG. 1.
Figure 5:
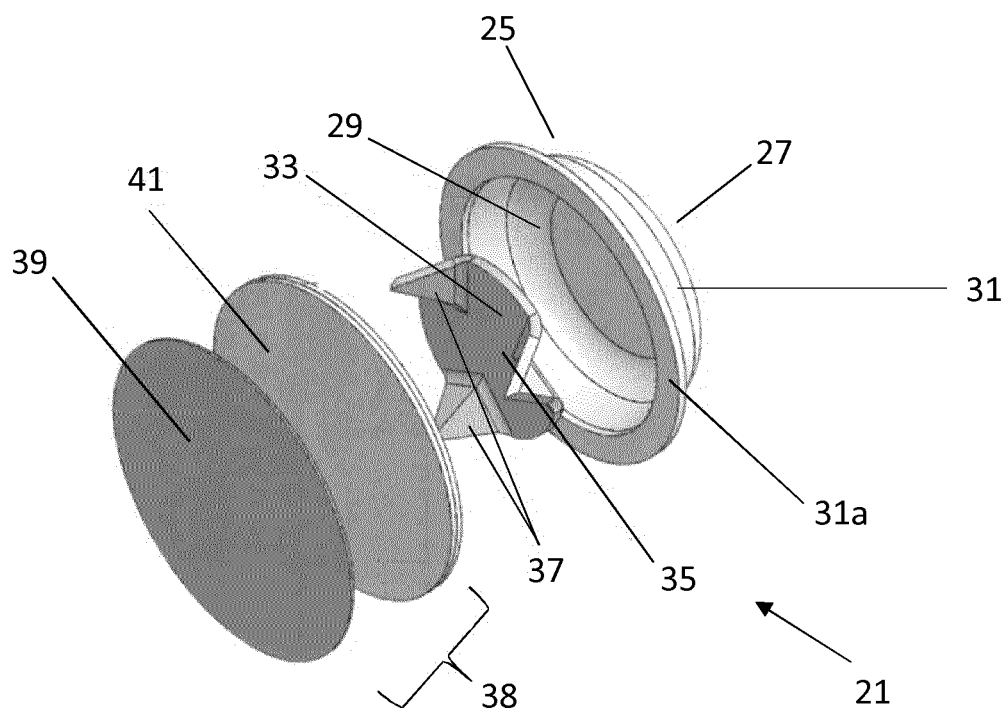
FIG. 5 shows an exploded view of an activating arrangement.

Referring now to FIGS. 4 and 5 in particular, in one example, the activating arrangement 21 comprises a flexible hollow cap 25, which for example is dome shaped, and which comprises a closed end 27, an open end 29 opposite the closed end 27, and a side wall 31 extending from the closed end 27 to the open end 29 and ending in a circumferential lip portion 31a. The activating arrangement 21 further comprises a piercing means 33 arranged within the interior of the hollow cap 25. In this example, the piercing means 33 comprises a generally planar base portion 35, fixed, for example glued, to an underside of the closed end 27 and one or more sharp formations 37 (3 are shown in this example) extending downwardly from the base portion 35. In this example, the activating arrangement 21 further comprises a rupturable barrier 38 which closes the open end 29 of the cap 25. As illustrated in FIG. 5, the rupturable barrier 38 may comprise at least a first layer 39 and a second layer 41 on top of the first layer 39. The first layer 39 is an adhesive layer that is used to attach the activating arrangement 21 to the exterior of the central section 7a of the outer tube 7 at a position where the activating arrangement covers an aperture that extends all of the way through the wall of the central section 7a and opens into the heat source chamber 17. The second layer 41, as will be explained in more detail below is a flexible layer that is capable of re-sealing after it has been ruptured by the piercing means 33.

To operate the activating arrangement 21, a user presses on the closed end 27 of the cap 25 which causes the cap 25 to flex towards the barrier 38 and hence causes the piercing means 33 to rupture the first layer 39 and the second layer 41 so that at least the tips of the formations 37 enter the heat source chamber 17 and contact the heat source material 19. In this way, the portion of the piercing means 33 that contacts the heat source material 19 acts as a heterogeneous nucleation region that initiates a phase change of the heat source material 19. As is known, nucleation is the process by which a phase change of a phase change material from liquid to solid is initiated and in heterogeneous nucleation, an insoluble foreign body, in this case the piercing means 33 acts as the centre upon which the first ions or molecules of the liquid phase change material become attached and oriented, rapidly attracting additional ions or molecules to form a solid crystal.

As the cap 25 relaxes back into its un-flexed shape, the piercing means 33 is pulled out of the heat source chamber 17 and back through the first layer 39 and the second layer 41. As already mentioned above, the second layer 41 is able to re-seal itself after having been ruptured once the piercing means 33 has passed back through it. For example, the second layer 41 may comprise an elastic material the resilience of which causes the second layer 41 to reseal after having been ruptured. The second layer 41 may, for example, be in the form of a rubber septum.

Accordingly, because the second layer 41 is self-sealing, the apparatus 1 can be used multiple times. After each usage, a user can reverse the phase change of the phase change material, for example, by immersing the device 1 in warm or hot water to change the phase of the material from solid back to liquid, and, if necessary, can re-charge the aerosol generating material 15 contained in the heating chamber 13. The apparatus 1 is then ready for use again.

In some examples, it is envisaged that when a user operates the activating arrangement 21, as the user re-leases their thumb or finger from pressing on the cap 25, the resilience of the cap 25 will cause the piercing means 33 to retract out of the heat source chamber 17 and free of the barrier 38 without being hindered by the phase change material 19.

The cap 25 may be made of any suitable material, for example, a thermoplastic, for example, formed Nylon.

The piercing means 33 can be formed of any suitable material or combination of materials including metals, alloys and plastics. In one example, the piercing means 33 comprises high carbon steel. It is preferred that there is more than one sharp formation 37 as this negates a need to orientate the piercing means 33 accurately in the cap 25 and makes it more likely that the barrier 38 will be successfully ruptures when the activating means 21 is operated.

The self-sealing layer 41 may comprise any suitable resilient material. The self sealing layer 41 may comprise two or more sub-layers at least one of which comprises a suitable resilient material. In one example, the resilient material comprises a thermoplastic, for example, silicone and/or a rubber based co-polymer.

Figure 6:
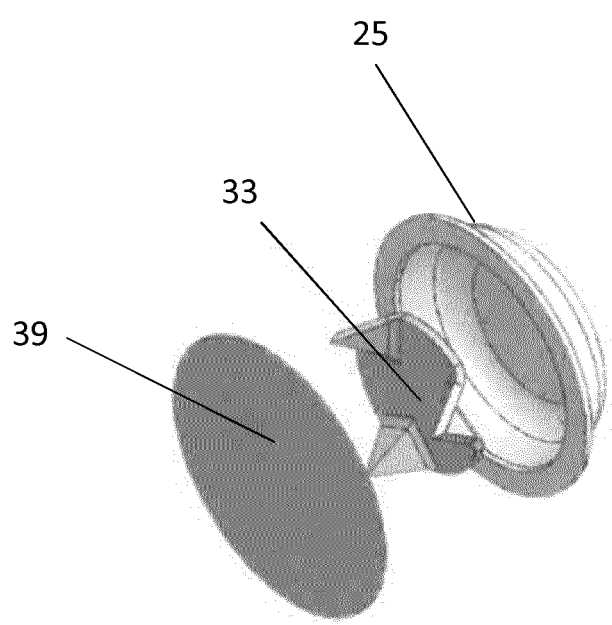
FIG. 6 shows an exploded view of an alternative activating arrangement.

In some examples, as is illustrated in FIG. 6, the barrier 38 comprises the adhesive layer 39 but not the re-sealable layer 41. In these examples, the apparatus 1 is a one-time use device only.

In this example, the piercing means 33 itself acts as activating agent for activating or inducing the phase change of the phase change material. In other examples, in addition to, or instead of the piercing means acting as the activating agent, the cap 25 may contain another activating agent that can contact the phase change material after the barrier has been ruptured. In some examples, this activating agent may be a solid comprising one or more of an ionic crystal such as a salt, for example, common salt NaCl, Chalk ($CaCO_3$), and a cellulose derivative, for example, Carboxymethyl Cellulose (CMC). The solid may comprise, for example, one or more crystals, for example, crystals of the phase change material itself, a coating or layer, powder, granules or be in a monolithic form, such as a molded or pressed tablet or similar form. In some examples, this activating agent may comprise a solid non-hygroscopic material, for example, metal filings such as iron, copper, aluminum or stainless steel filings.

In the above example, the piercing means 33 is part of the apparatus 1. In an alternative, the apparatus 1 is not provided with the cap 25 or the piercing means 33 and instead an additional device (not illustrated) may be provided and which comprises a retractable piercing means and into which or next to which device, for example, a user can place the apparatus 1, so that the device's piercing means can be used to pierce the barrier 38 in order to initiate the phase change of the phase change material 19.

Figure 7:
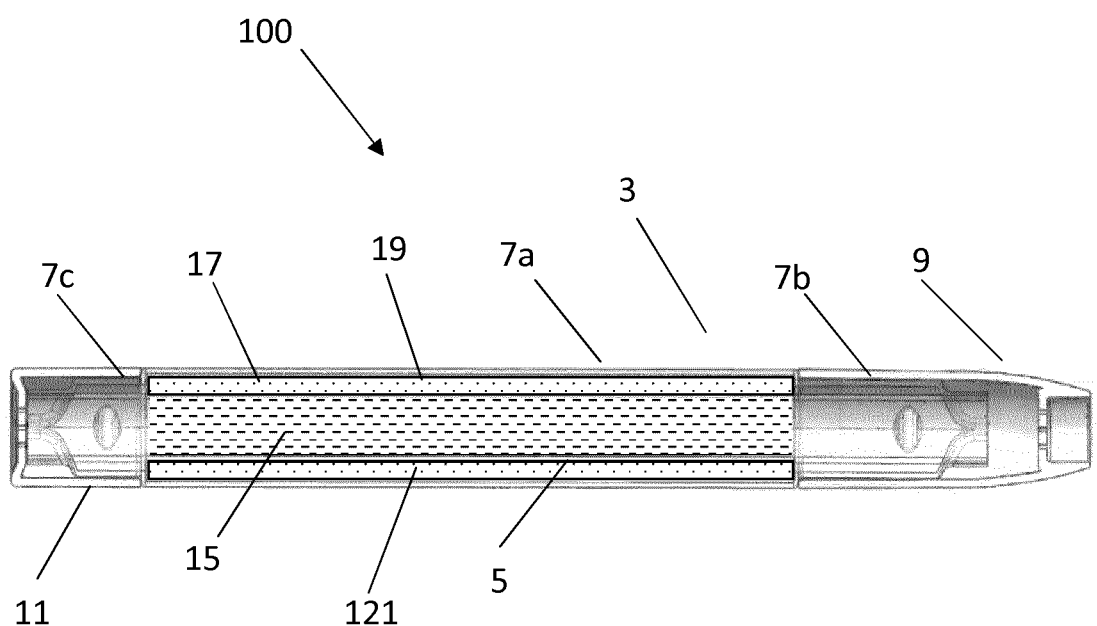
FIG. 7 shows a cross-sectional side view of another example of an apparatus for heating an aerosol generating material.

Referring now to FIG. 7, there is illustrated, another example of an apparatus 100 arranged to heat aerosol generating material 15. In many aspects, the apparatus 100 is identical to the apparatus 1 described above and like features have been identified using like reference numerals and in the interests of brevity will not be described in detail again.

In this example, the apparatus 100 does not comprise an activating arrangement that is located externally to the heat source chamber 17 (as is the case with the apparatus 1) but instead comprises an activating arrangement that comprises an activating agent 121 (represented in FIG. 7 by dots) that when the apparatus 100 is agitated, for example, shaken, flicked, tapped or squeezed, initiates the phase change of the phase change material 19.

Figure 8:
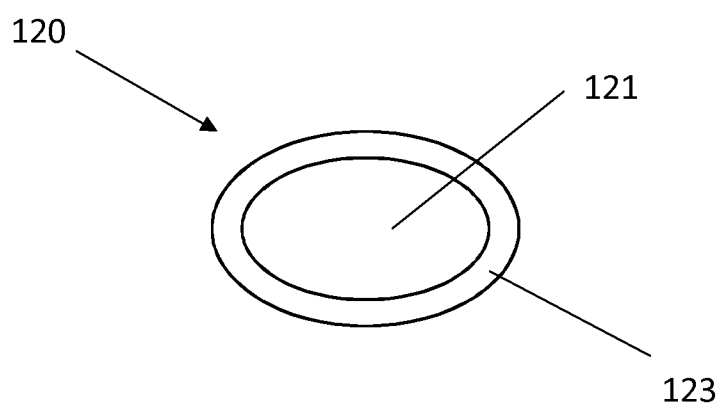
FIG. 8 shows a schematic cross-sectional view of a capsule for use in an activating arrangement for the apparatus shown in FIG. 7.

As illustrated in FIG. 8, in one example, the activating agent 121 comprises one or more capsules 120 each comprising a core 121 surrounded by a protective membrane 123. The protective membrane 123 isolates the core 121 from the phase change material 19 and comprises a material that inhibits the capsule 120 from acting as a nucleation zone for initiating a phase change of surrounding phase change material 19. The material may, for example, comprise an inert plastic based membrane. In contrast, the core 121 comprises a material that does act as a nucleation zone for initiating a phase change of surrounding phase change material 19. The protective membrane 123 material is relatively breakable so that when the apparatus 100 is agitated, for example, shaken or tapped or squeezed, the protective membrane 123 of one or more of the capsules 120 ruptures, for example, as a result of capsules 120 contacting each other or contacting walls of the apparatus 1. The rupturing exposes the core 121 of the one or more capsules 120 to the phase change material so that each exposed core 121 acts a nucleation site that initiates the phase change of the phase change material 19.

In one example, each capsule 120 is a micro-capsule (i.e. has a diameter on order of microns in size) and the activating agent 121 comprises a large number of such micro-capsules, for example, on the order of thousands, suspended in the phase change material 19. During manufacturing of the apparatus 100, the micro-capsules may be mixed within the main solution of the phase change material and hot filled into the apparatus 100.

On first usage, agitating the apparatus 100 causes some of the micro-capsules to rupture which initiates the phase change of the phase change material, but many of the micro-capsules remain intact. Consequently, once the phase change of the phase change material has been reversed, the apparatus 100 can be re-used. The apparatus 100 can be repeatedly re-used in this way, the exact number of re-uses depending upon the number of micro-capsules initially included in phase change material 19.

The core 121 of a capsule may comprise any suitable solid material, for example a metal or salt. In one example, the core 121 comprises a solid crystal of the phase change material, for example, a solid crystal of a hydrated salt such as the ones described above.

The capsules may be shaped in such a way so as to enhance their rupturability. For example, the capsules may be roughly oval shaped and the membrane 123 may be thinner towards the end points of the capsules.

In one example an additional electronic or mechanical device (not illustrated) may be provided in which a user can place the apparatus 100, and which vibrates the apparatus 100 to cause capsules 120 to rupture to initiate the phase change.

In an alternative example, the apparatus 100 does not comprise any capsules 120 and the vibrations and the vibrations caused by the additional electronic or mechanical device are sufficient to induce a phase change in the phase change material 19.

Figure 9:
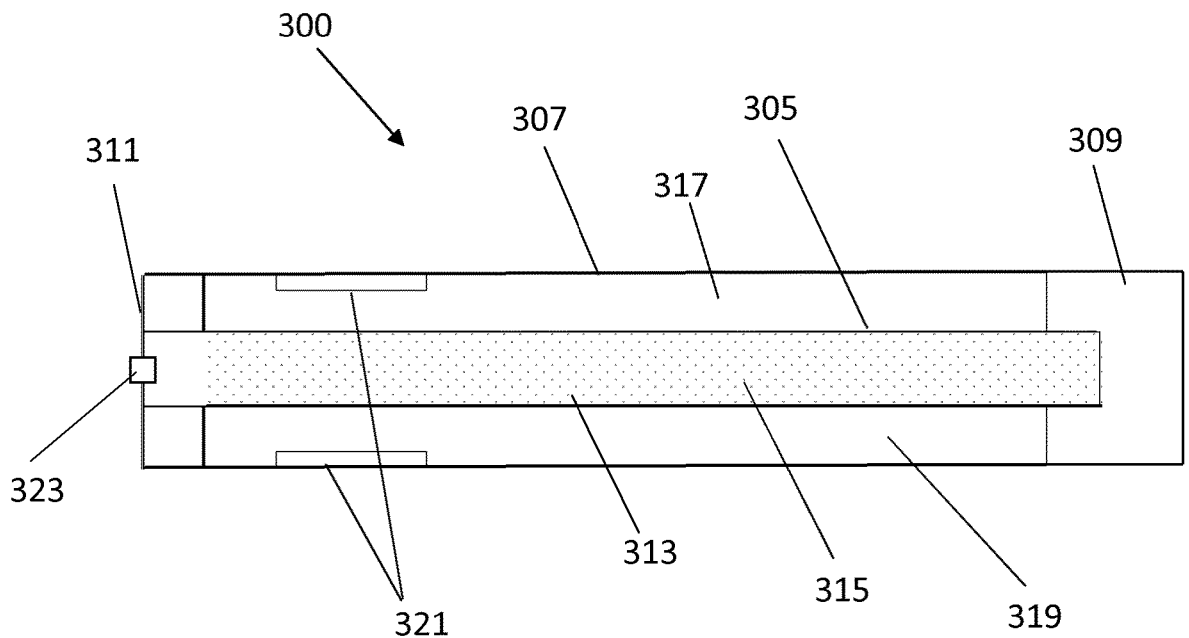
FIG. 9 shows a cross-sectional side view of another example of an apparatus for heating an aerosol generating material.

Referring now to FIG. 9, there is shown a schematic illustration of another apparatus 300, in some respects similar to those discussed above, arranged to heat aerosol generating material to volatize at least one component of the aerosol generating material.

The apparatus 300 in this example is generally elongate and comprises an inner tube 305, an outer tube 307, a mouthpiece 309 and an end cap 311. The inner tube 305 is arranged generally concentrically and coaxially inside the outer tube 307. The outer tube 307 is sealed at both its ends, for example by heat sealing, against the inner tube 307 so that the outer tune 307 is a closed tube. In contrast, the inner tube 305 is open at both ends. The mouth piece 309 fits over the end of the inner tube 305 at the front of the apparatus 300 and the end cap 311 fits over the end of the inner tube 305 at the back of the apparatus 300.

The apparatus 300 may comprise any suitable material or materials, similar to those already discussed above with respect to the apparatus 1.

The interior of inner tube 305 acts as a heating chamber 313 for containing aerosol generating material 315 to be heated and volatized. The heating chamber 313 is in fluid flow communication with the mouthpiece 309 and the end cap 311. The generally annular region defined by the outer tube 307 and the inner tube 305 acts as a heat source chamber 317 that contains a heat source material 319 that can be activated to generate heat in order to heat the heating chamber 313 and consequently the aerosol generating material 315 contained in the heating chamber 313.

The aerosol generating material 315 and heat source material 319 may comprise any of the corresponding materials already described above with respect to the apparatus 1. The end cap 311 has one or more air inlets 323 formed therein so that, again, in use, as a user inhales on the mouth piece 309, air is drawn into the heating chamber 313 through the one or more air inlets 323 formed in the end cap 311 and a combination of the drawn air and aerosol and/or gas or vapor passes through the heating chamber 313 and enters the mouthpiece 309 for inhalation by the user.

In this example, the apparatus 300 comprises an activating arrangement 321 that comprises an electric charge generator for generating an electric charge and/or current that exposed to the phase change material 319 in order to activate a change of phase of the phase change material 319.

As is illustrated in FIG. 9, the electric charge generator 321 may comprise one or more portions of piezo-electric material, for example piezo-electric crystals, positioned in the heat source chamber 317, for example, attached to the inside wall of the outer tube 307, in contact with the phase change material 319. When the one or more portions 321 of piezo-electric material are deformed, by example, by a user squeezing the outer tube 307 in the vicinity of the portions 321 of piezo-electric material, the portions 321 of piezo-electric material generate a voltage and hence an electrical charge and/or current which initiates the phase change of the phase change material 319. For example, the one or more portions 321 of piezo-electric material may generate an electrical spark that passes through the phase change material 319 and initiates the phase change.

In an alternative example, the electric charge generator 321 may comprise one or more capacitors positioned in the heat source chamber 317, for example, attached to the inside wall of the outer tube 307, in contact with the phase change material 319 and a power supply (not shown) for charging the one or more capacitors. A user may activate the power supply, for example by pushing a button (not shown), to charge the one or more capacitors so that electrical charge that forms on the one or more capacitors or electrical current passes from the one or more capacitors into the phase change material 319 and initiates the phase change of the phase change material 319.

In another example, the activating arrangement may comprises means arranged in the heat source chamber which can be operated to vibrate to cause vibrations in the phase change material in order to initiate the phase change. The means may comprise on or more resonators configured to resonate at or around the resonant frequency of the phase change material to generate corresponding vibrations in the phase change material. A power source may be provided to power the resonators.

Figure 10:
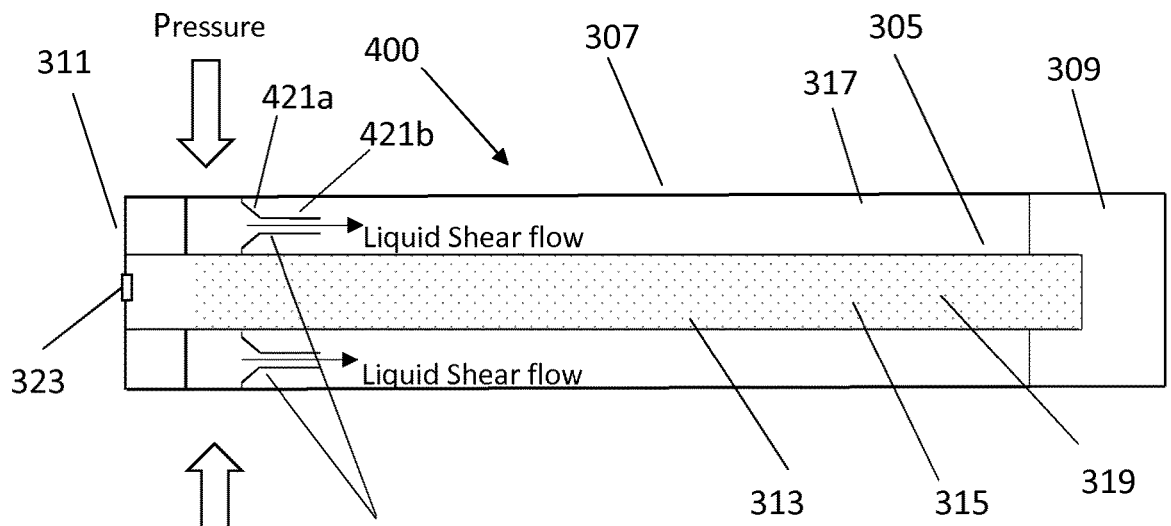
FIG. 10 shows a cross-sectional side view of another example of an apparatus for heating an aerosol generating material.

Referring now to FIG. 10, there is shown a schematic illustration of another apparatus 400 which in many aspects is the same as the apparatus 300 but which has a different activating arrangement 421 to that of the apparatus 300. Features of the apparatus 400 that are the same as corresponding features of the apparatus 300 have been identified using the same reference numerals and in the interests of brevity will not be described in detail again.

In the example of FIG. 10, the activating arrangement 421 comprises one or more arrangements for generating liquid shear in the phase change material 319 to induce a liquid to solid phase change of the phase change material 319. In this example, the activating arrangement 421 comprises one or more funnels 421 located in the heat source chamber 317 towards the back of the apparatus 400. Each funnel 421 is located between the inner wall of the outer tube 307 and the outer wall of the inner tube 305. Each funnel 421 comprises a conical head portion 421a that tapers from a wide aperture to a narrow aperture and a tube portion 421b that extends from the narrow aperture parallel with the longitudinal axis of the apparatus 400. The diameter of the tube portion 421b is substantially smaller than the perpendicular distance between the outer tube 307 and the inner tube 305. In use, a user compresses the outer tube 307 in the regions indicated by the large arrows which forces phase change material to flow through each funnel 421 from the wide aperture and through the tube portion 421b as indicated by the smaller arrows. Flowing through the relatively narrow tube portion 421 causes liquid shearing in the phase change material and this liquid shearing initiates the phase change of the phase change material from the liquid to the solid state.

It will be appreciated that the described arrangement is exemplary only, and many other types of activating arrangement that can cause liquid shearing in the phase change material 319 to initiate the phase change may be used.

In yet another example, an activating arrangement may be operated to initiate a phase change by causing localized cooling in one or more regions of the phase change material in the heat source chamber. For example, the activating arrangement may achieve this by letting compressed gas expand into the one or more regions.

Figure 11A:
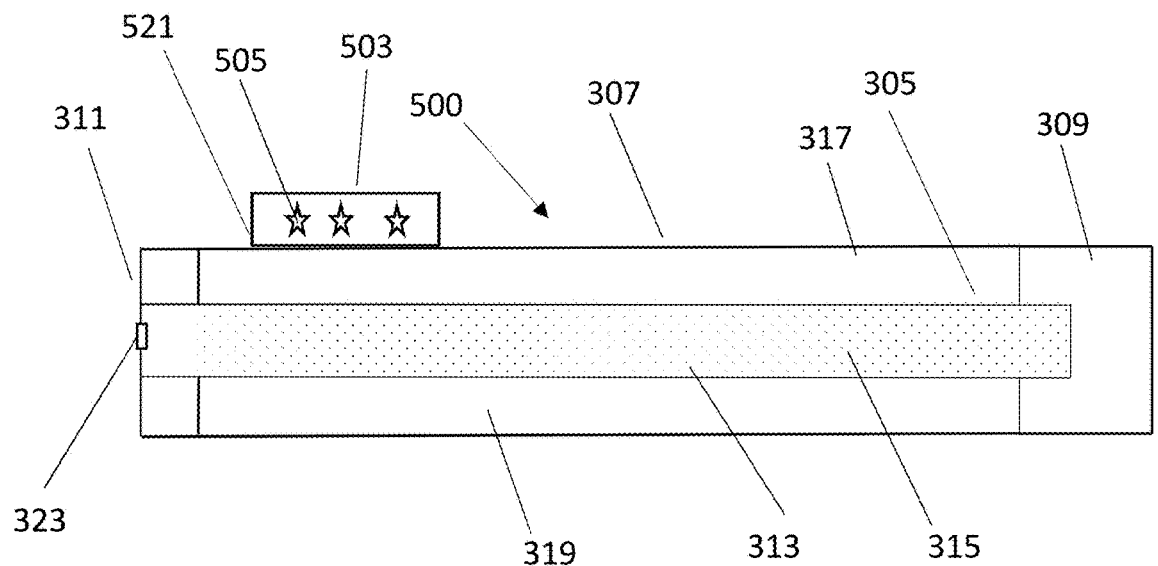
FIG. 11a shows a cross-sectional side view of another example of an apparatus for heating an aerosol generating material having an activating arrangement in a first configuration.
Figure 11B:
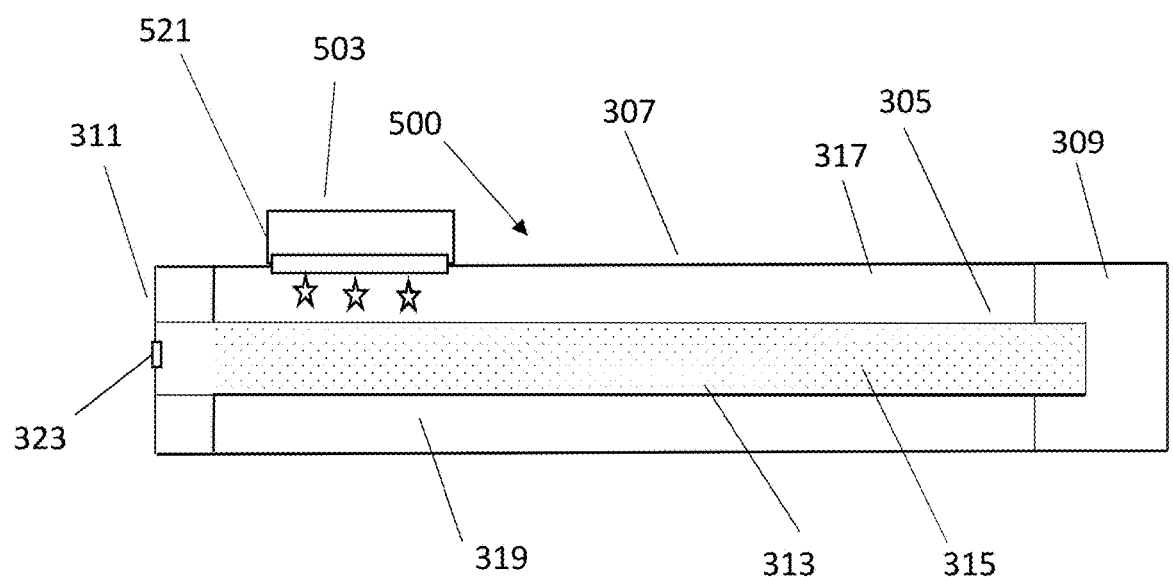
FIG. 11b shows a cross-sectional side view of the apparatus shown in FIG. 11b with the activating arrangement in a second configuration.

Referring now to FIGS. 11a and 11b, there is shown schematic illustrations of another apparatus 500 which in many aspects is the same as the apparatus 300 but which has a different activating arrangement 521 to that of the apparatus 300. Features of the apparatus 500 that are the same as corresponding features of the apparatus 300 have been identified using the same reference numerals and in the interests of brevity will not be described in detail again.

In the example of FIGS. 11a and 11b, the activating arrangement 521 comprises a compartment 503 containing an activating agent 505. The activating arrangement 521 is configurable in a closed configuration, illustrated in FIG. 11a, in which an opening in the compartment 503 and an opening in the heat source chamber 317 are misaligned and in an open configuration, illustrated in FIG. 11b, in which the opening in the compartment 503 and the opening heat source chamber 317 are aligned. In the closed configuration the phase change material 319 is sealed in the heat source chamber 317 and the activating agent 505 is sealed in the compartment 503. In the open configuration, the heat source chamber 317 and the compartment 503 are open to each other so that the activating agent 505 can come into contact with the phase change material 319 to initiate the phase change of the phase change material 319.

The activating arrangement 521, or one or more parts of it, may be moved, for example rotated, slid, or otherwise translated from one position another to configure the activating arrangement 521 between the closed and open configurations.

In one example, the activating agent 505 may comprise one or more seed particles that can be released into the heat source chamber 317, for example, by tapping or shaking the apparatus 500, when the activating arrangement 521 is in the open configuration. The seed particles may for example comprise solid crystals of the phase change material 319.

In one example, rather comprises a specific activation arrangement of any of the types described above, an apparatus otherwise similar to the apparatuses described herein may be placed in a fridge or freezer to increase the viscosity of the phase change material in order to initiate a phase change.

Although in the examples described above, the phase change material generates heat when undergoing its phase change to heat material in the heating chamber, in alternative examples, the phase change material may absorb heat when undergoing its phase change to cool material in a cooling chamber. The material, for example, may be a drink or a foodstuff best consumed chilled.

In an alternative example, the activating agent 505 comprises a plunger or the like that can moved between a retracted position when the activating arrangement 521 is in the closed configuration and an extended position when the activating arrangement 521 is in the open configuration. When in the extended position the plunger extends from the compartment 503 into the heat source chamber 317 to contact the phase change material to initiate the phase change. The plunger may be made to oscillate, for example by a user flicking or otherwise moving it back and forth, within the heat source chamber 317 to facilitate initiating the phase change.

Embodiments of the disclosure are configured to comply with applicable laws and/or regulations, such as, by way of non-limiting example, regulations relating to flavors, additives, emissions, constituents, and/or the like. For example, the invention may be configured such that a apparatus implementing the invention is compliant with applicable regulations before and after adjustment by a user. Such implementations may be configured to be compliant with applicable regulations in all user-selectable positions. In some embodiments, the configuration is such that a apparatus implementing the invention meets or exceeds required regulatory test(s) in all user-selectable positions, such as, by way of non-limiting example, the testing threshold(s)/ceiling (s) for emissions and/or smoke constituents.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc, other than those specifically described herein. In addition, this disclosure may include other inventions not presently claimed, but which may be claimed in future.

The invention claimed is:

1. An apparatus for heating or cooling a material to be heated or to be cooled, the apparatus comprising:
   a first compartment for containing the material to be heated or to be cooled;
   a second compartment containing a phase change material, wherein the phase change material is either for generating heat to heat the first compartment or absorbing heat to cool the first compartment when undergoing a phase change; and
   an activating arrangement comprising a phase change activating agent and a barrier that separates the phase change activating agent from the phase change material, wherein the activating arrangement is configured to cause the barrier to rupture when operated so that the phase change activating agent contacts the phase change material in order to activate a change of phase of the phase change material, and wherein the barrier is configured to re-seal after being ruptured.

2. The apparatus as claimed in claim 1, wherein the barrier comprises a resilient material that is able to resiliently re-seal after being ruptured.

3. The apparatus as claimed in claim 1, wherein the activating arrangement comprises one or more pointed protrusions for piercing the barrier when the activating arrangement is operated.

4. The apparatus as claimed in claim 3, wherein the activating arrangement comprises a flexible hollow body attached to the second compartment and which contains the one or more pointed protrusions and the activating agent, and wherein the activating arrangement is configured to be operated by pressing the flexible hollow body to cause the one or more pointed protrusions to rupture the barrier.

5. The apparatus as claimed in claim 3, wherein the one or more pointed protrusions are the activating agent and/or carry the activating agent.

6. The apparatus as claimed in claim 1, wherein the barrier comprises an adhesive layer for adhering the activating arrangement to the second compartment.

7. The apparatus as claimed in claim 1, wherein the activating arrangement comprises an opening that is aligned with an opening of the second compartment and wherein the barrier seals both openings.

8. The apparatus as claimed in claim 1, the apparatus further comprising a first tube and a second tube, wherein the second tube is arranged co-axially within the first tube, wherein the first tube defines the first compartment and wherein the first tube and the second tube between them define the second compartment.

9. The apparatus as claimed in claim 1, wherein the phase change material is for generating heat to heat the first compartment, and wherein the first compartment contains material for generating aerosol when heated, the apparatus further comprising a mouthpiece that is in fluid communication with the first compartment and through which aerosol generated by the material when the material is heated can be inhaled.

10. The apparatus as claimed in claim 9, wherein the material for generating aerosol when heated comprises tobacco or a tobacco based product.

* * * * *